United States Patent [19]
Whitmore

[11] Patent Number: 5,674,394
[45] Date of Patent: Oct. 7, 1997

[54] SINGLE USE SYSTEM FOR PREPARATION OF AUTOLOGOUS PLASMA

[75] Inventor: Elaine Whitmore, Arlington, Tex.

[73] Assignee: Johnson & Johnson Medical, Inc., Arlington, Tex.

[21] Appl. No.: 410,028

[22] Filed: Mar. 24, 1995

[51] Int. Cl.$^6$ .................... B01D 61/18; B01D 63/02; B01D 65/00

[52] U.S. Cl. .................... 210/321.8; 210/321.6; 210/321.79; 210/321.88; 210/321.89; 210/416.1; 210/433.1; 210/500.23; 422/99; 422/101; 422/102; 436/177; 436/178

[58] Field of Search .................... 210/321.6, 321.79, 210/321.8, 321.88, 321.89, 416.1, 433.1, 435, 497.01, 500.23; 422/99, 101, 102; 436/177, 178; 604/187

[56] References Cited

U.S. PATENT DOCUMENTS

| | | | |
|---|---|---|---|
| Re. 32,089 | 3/1986 | Blatt et al. | 210/651 |
| 3,228,876 | 1/1966 | Mahon . | |
| 3,616,928 | 11/1971 | Rosenblatt . | |
| 3,962,094 | 6/1976 | Davis et al. | 210/321.79 |
| 4,124,509 | 11/1978 | Iijima et al. | 210/456 |
| 4,125,468 | 11/1978 | Joh et al. | 210/456 |
| 4,362,567 | 12/1982 | Schwarz et al. | 106/157 |
| 4,430,213 | 2/1984 | Ishikawa | 210/416.1 |
| 4,440,641 | 4/1984 | Ostertag | 210/321.79 |
| 4,587,018 | 5/1986 | Blomback et al. | 210/484 |
| 4,588,407 | 5/1986 | Isono et al. | 210/646 |
| 4,696,748 | 9/1987 | Nitadori et al. | 210/500.23 |
| 4,708,796 | 11/1987 | Yoshimoto et al. | 210/321.8 |
| 4,720,342 | 1/1988 | Takemura et al. | 210/321.79 |
| 4,735,726 | 4/1988 | Duggins | 210/651 |
| 4,770,778 | 9/1988 | Yokoyama et al. | 210/321.79 |
| 4,789,473 | 12/1988 | Mathieu et al. | 210/321.8 |
| 4,869,822 | 9/1989 | Kamei et al. | 210/321.79 |
| 4,888,109 | 12/1989 | Manohar | 210/94 |
| 4,892,710 | 1/1990 | Wong et al. | 422/102 |
| 4,895,805 | 1/1990 | Sato et al. | 210/416.1 |
| 4,915,832 | 4/1990 | Bernd et al. | 210/321.8 |
| 4,959,152 | 9/1990 | Nichols | 210/651 |
| 4,966,699 | 10/1990 | Sasaki et al. | 210/321.8 |
| 4,975,187 | 12/1990 | Espenan | 210/321.89 |

(List continued on next page.)

FOREIGN PATENT DOCUMENTS 0 438 196  7/1991  European Pat. Off. .

OTHER PUBLICATIONS

Microgon Ultrafiltration Modules for Bench-Scale to Process-Scale Molecular Separations Microgon Inc. TSB 8-0477 Feb. 1993.

Evaluation of a New Filter for Membrane Plasma Separation, Mauro Valbonesi et al., La Ricerca Clin. Lab. 13, 479, 1983, pp. 479-485.

Plasma Separation Using a Hollow Fiber Membrane Device, D.H. Buchholz et al., Transfusion, vol. 26, No. 2, 1986, pp. 145-150.

Autologous Fibrin Gel: Bactericidal Properties in Contaminated Hepatic Injury, Scott A. Dulchavsky, M.D., et al., The Journal of Trauma, 1991 by the Williams & Wilkins Co., pp. 991-995, vol. 31, No. 7.

(List continued on next page.)

*Primary Examiner*—John Kim
*Attorney, Agent, or Firm*—Andrew C. Farmer

[57] ABSTRACT

A system for preparing autologous plasma comprises a single use filter unit having two inlets in fluid communication with each other, an outlet, and a filtration membrane selectively permeable to blood plasma separating the inlets from the outlet. Manually operable, single use pumps, preferably syringes, connect to the inlets. A flow path is defined along the membrane between the pumps, whereby, whole blood can be repeatedly exchanged between the two pumps, past the membrane, to cause plasma to flow across the membrane and out of the outlet. A syringe can collect plasma from the outlet. Plasma thus collected can be simultaneously applied with a thrombin solution to a site on the body, thereby forming a fibrin gel.

6 Claims, 3 Drawing Sheets

U.S. PATENT DOCUMENTS

| | | | |
|---|---|---|---|
| 4,995,967 | 2/1991 | van Driessche | 210/94 |
| 5,002,668 | 3/1991 | Spranger | 210/321.79 |
| 5,008,012 | 4/1991 | Hagihara et al. | 210/321.8 |
| 5,030,215 | 7/1991 | Morse et al. | 604/410 |
| 5,037,610 | 8/1991 | Fukasawa et al. | 210/321.81 |
| 5,055,198 | 10/1991 | Shettigar | 210/650 |
| 5,100,549 | 3/1992 | Langerak et al. | 210/321.8 |
| 5,104,375 | 4/1992 | Wolf et al. | 604/56 |
| 5,122,113 | 6/1992 | Hattler | 604/26 |
| 5,169,529 | 12/1992 | Carroll et al. | 210/321.78 |
| 5,215,519 | 6/1993 | Shettigar | 604/4 |
| 5,219,328 | 6/1993 | Morse et al. | 604/49 |
| 5,226,877 | 7/1993 | Epstein | 604/35 |
| 5,266,197 | 11/1993 | Takata et al. | 210/500.23 |
| 5,271,743 | 12/1993 | Hattler | 604/26 |
| 5,318,524 | 6/1994 | Morse et al. | 604/82 |
| 5,322,800 | 6/1994 | Murphy | 210/416.1 |
| 5,464,535 | 11/1995 | Shettigar | 210/321.89 |
| 5,496,473 | 3/1996 | Chow | 210/635 |

OTHER PUBLICATIONS

Antibiotic–Primed Fibrin Gel Improves Outcome in Contaminated Splenic Injury, Richard D. Ing et al., The Journal of Trauma, 1992 by Williams & Wilkins, pp. 118–119, vol. 33, No. 1.

A Simple Method of Preparation of Autologous Fibrin Glue by Means of Ethanol, Henrik K. Kjaergard, et al, Surg. Gynecol. Obstet. Jul. 1992, 175 (1) pp. 72–73.

SINGLE USE SYSTEM FOR PREPARATION OF AUTOLOGOUS PLASMA

BACKGROUND OF THE INVENTION

1. Field of the Invention

The present invention relates to a system for obtaining autologous plasma from a patient during surgery. The invention further relates to a method for preparing fibrin gel and other hemostat or tissue sealant preparations from the autologous plasma.

2. Background Information

Preparations of human coagulation factors including fibrinogen and thrombin, have been used extensively in surgery over the last ten years. These biological fibrin sealants (also known as fibrin glue, fibrin adhesive, or fibrin tissue sealant) promote hemostasis and wound healing by sealing leakage from tissues, sutures, staples, and prostheses and are particularly useful during open heart surgery in heparinized patients. The sealants also have limited use as an adhesive for the bonding of tissues and they reduce the amount of blood required for transfusions by controlling intraoperative bleeding. Their effectiveness is reflected in the extensive range of surgical applications for which they have been used, including cardiovascular surgery, plastic surgery, orthopedics, urology, obstetrics and gynecology, dentistry, maxillofacial and ophthalmic surgery.

Fibrin sealant products can be prepared from pooled human plasma. However, such preparations potentially risk transmission of HIV, hepatitis B and other serologically transmitted illnesses. Also, in some instances these preparations could cause immunologic reactions.

As an alternative, some hospitals are preparing fibrin sealant in-house using the patient's own blood (autologous) or single-donor (homologous) plasma as a source of fibrinogen and Factor XIII. The components are typically prepared by freezing plasma at temperatures below −20° C. overnight, slowly thawing the material at 0°–4° C., centrifuging, and transferring the cryoprecipitate to a syringe or spray container. The procedure usually requires several hours, making the product unavailable for emergency cases. The lengthy manipulations currently required to generate fibrin sealant also introduce the risk of contaminating the product and transmitting viral infections to the technicians involved.

The thrombin, usually purified from bovine plasma, can be obtained commercially and is typically prepared in a separate syringe or spray container. The two solutions are delivered simultaneously or alternately to generate fibrin sealant at the site of the wound.

The hemostatic efficacy of fibrin glue has been well established. Autologous fibrin gel, made from plasma rather than a fibrinogen-containing precipitate, appears to have comparable hemostatic properties to traditional fibrin glue as well as valuable sealant properties. For instance, fibrin gel is useful in sealing air leaks in pulmonary procedures.

In preparing fibrin gel, plasma is typically obtained from autologous blood following centrifugation for about ten minutes to separate blood cells from anticoagulated blood, followed by removal of the plasma. Centrifugation in the operating room, however, may be inconvenient because of the required instrumentation, potential for aerosolization with its concomitant contamination risks, and difficulty in decontaminating instrumentation between procedures. If centrifugation takes place external to the OR, aseptic transport of the plasma fraction to the operative site is required.

Hollow fiber devices permitting separation of plasma from blood without the need for centrifugation have been used for plasma exchange therapy (PET). In PET, the separated plasma is eliminated and the separated blood cells with replacement fluids are returned to the patient.

Recently, hollow fiber filtration technology has been developed to meet the requirements of cell separation from cell cultures—including shear-sensitive mammalian cells—while allowing free passage of soluble proteins. This membrane technology offers an alternative to centrifugation, precipitation and conventional filtration techniques for bioseparations, eg. the processing of fermentation products, and is available for small volume applications. Sterilizable, disposable filtration modules are available from at least one manufacturer.

SUMMARY OF THE INVENTION

The described invention uses compact, small-volume disposable filtration technology to separate plasma from blood. In contrast to PET applications, the separated blood cells trapped by the filter are disposed of along with the filter. The separated plasma is used as a source of autologous material—eliminating the risk of cross-infection of immunological consequences. Preparation of the plasma requires no instrumentation and can be performed quickly and conveniently at the time and location of the surgical or medical procedure for which the material will be used. Specific uses for the autologous plasma obtained in this manner include preparation of fibrin gel and other hemostatic/tissue sealant formulations based on proteins and or clotting factors.

A single use system for obtaining autologous plasma according to the present invention comprises a plasma separator for separating plasma from whole blood. The plasma separator comprises a single use filter unit having a first inlet and a second inlet in fluid communication with each other, an outlet, and a filtration membrane separating the inlets from the outlet. The filtration membrane is selectively permeable to blood plasma. A manually operable, single use first pump comprises a receiving chamber connected to the first inlet. The receiving chamber has a manually moveable wall for altering the volume of its receiving chamber. A manually operable, single use second pump comprises a receiving chamber connected to the second inlet and a manually moveable wall for altering the volume of its receiving chamber. A flow path is defined along the membrane between the first and second pumps. Thereby, whole blood can be repeatedly exchanged between the receiving chambers in the first and second pumps, past the membrane, to cause plasma to flow across the membrane and out of the outlet.

Preferably, the membrane comprises one or more hollow fibers, each of the one or more fibers having a lumen therethrough, and the flow path extends through the lumens of the one or more fibers. Also preferably, the filter unit comprises an elongated housing having a first end and a second end with the one or more hollow fibers extending axially therethrough. Each of the one or more fibers has an outer surface, the housing has an inner surface and an interior space is thus formed between the outer surfaces of the fibers and the inner surface of the housing. Pottings at the first and second ends of the housing secure the fibers therein and separate the lumens from the interior space. The first pump connects to the housing first end and the second pump connects to the housing second end, each with its respective receiving chamber in fluid communication with the lumens of the hollow fibers. The outlet is in fluid communication with the interior space whereby when the blood is pumped through the lumens of the hollow fibers by the first and second pumps, the plasma flows through the membrane into the interior space of the housing and out of the outlet. Preferably, the first and second pumps comprise syringes. A collection syringe preferably connects to the outlet for receiving the plasma.

The system can further comprise an applicator for preparing and applying fibrin gel in a medical procedure. The applicator comprises a first injector containing a thrombin solution, a second injector containing the plasma, the plasma containing an amount of fibrinogen, and a manifold in communication with the first and second injectors for applying the thrombin solution and plasma simultaneously to a site on a body. Preferably, the first and second injectors comprise syringes. Also, the syringe forming the second injector is preferably the collection syringe.

The system can be provided in a sealed sterile package containing the plasma separator and the fibrin applicator; and instructions for obtaining whole blood from a patient in the first syringe, manually pumping the whole blood in alternating fashion between the first and second syringes and collecting plasma from the whole blood in the collection syringe, and simultaneously applying the plasma thus collected along with a solution of thrombin to a site on a body.

A method, according to the invention, for preparing fibrin gel from autologous plasma comprises the steps of: extracting a quantity of blood from a patient; providing a single use filter unit having first and second inlets and an outlet; providing first and second manually operable pumps, each having a receiving chamber with a manually moveable wall; placing the receiving chambers of the first and second pumps into fluid communication with the first and second inlets, respectively; disposing a membrane selectively permeable to blood plasma between the first and second inlets, thereby forming a flow path along the membrane between the first and second inlets and isolating them from the outlet; alternatingly and manually moving the moveable walls in the first and second pumps to provide an alternating flow between the first and second inlets along the membrane; passing the plasma through the membrane to an outlet of the filter unit; collecting the plasma; and disposing of the filter unit.

The method preferably further comprises the steps of mixing the plasma with thrombin to form fibrin gel and applying the fibrin gel to a site on a body. Preferably, the plasma and a solution containing the thrombin are simultaneously applied to the body site to form the fibrin gel.

DETAILED DESCRIPTION

Figure 1:
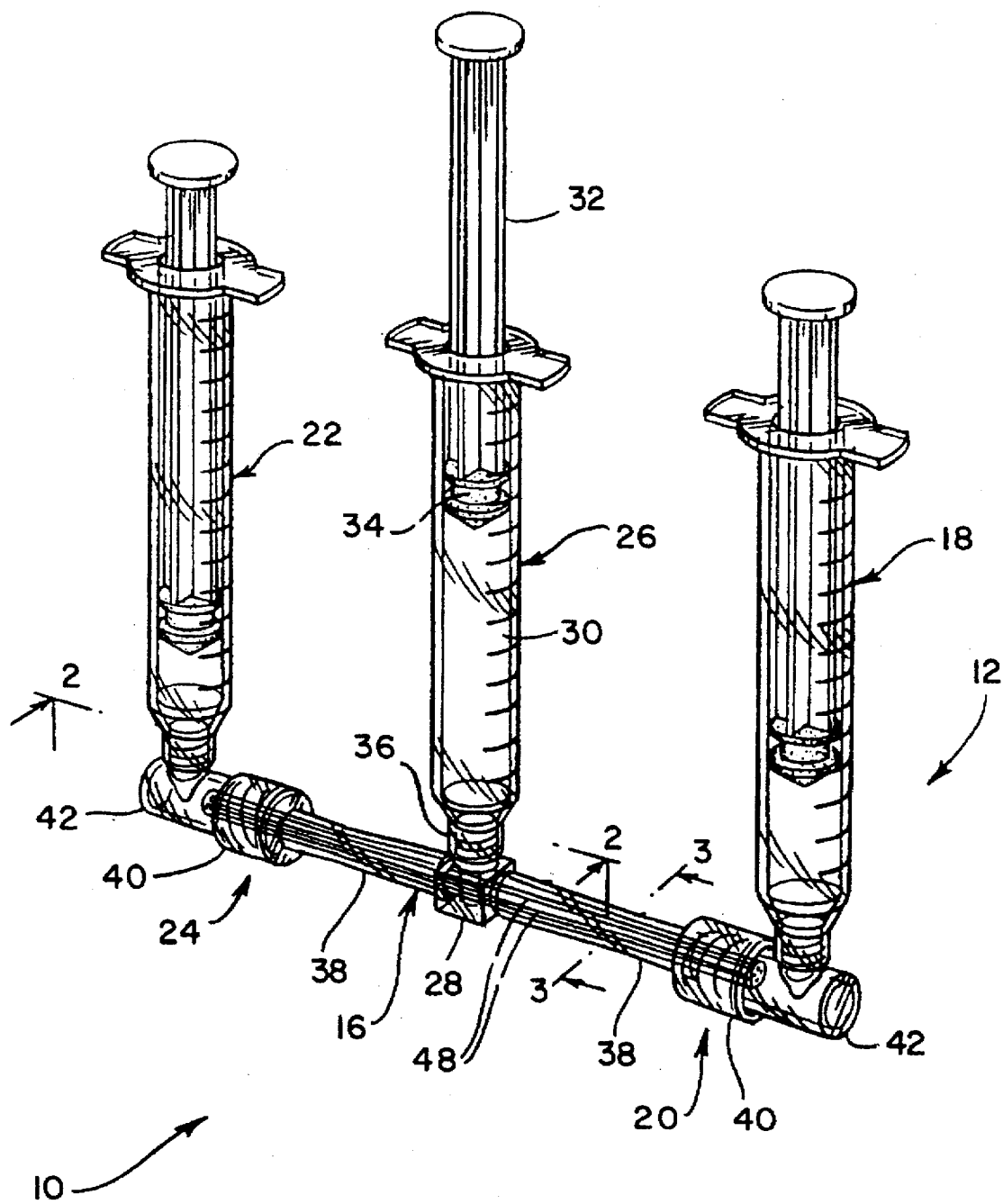
FIG. 1 is a perspective view of a filter for preparing autologous plasma according to the invention.
Figure 4:
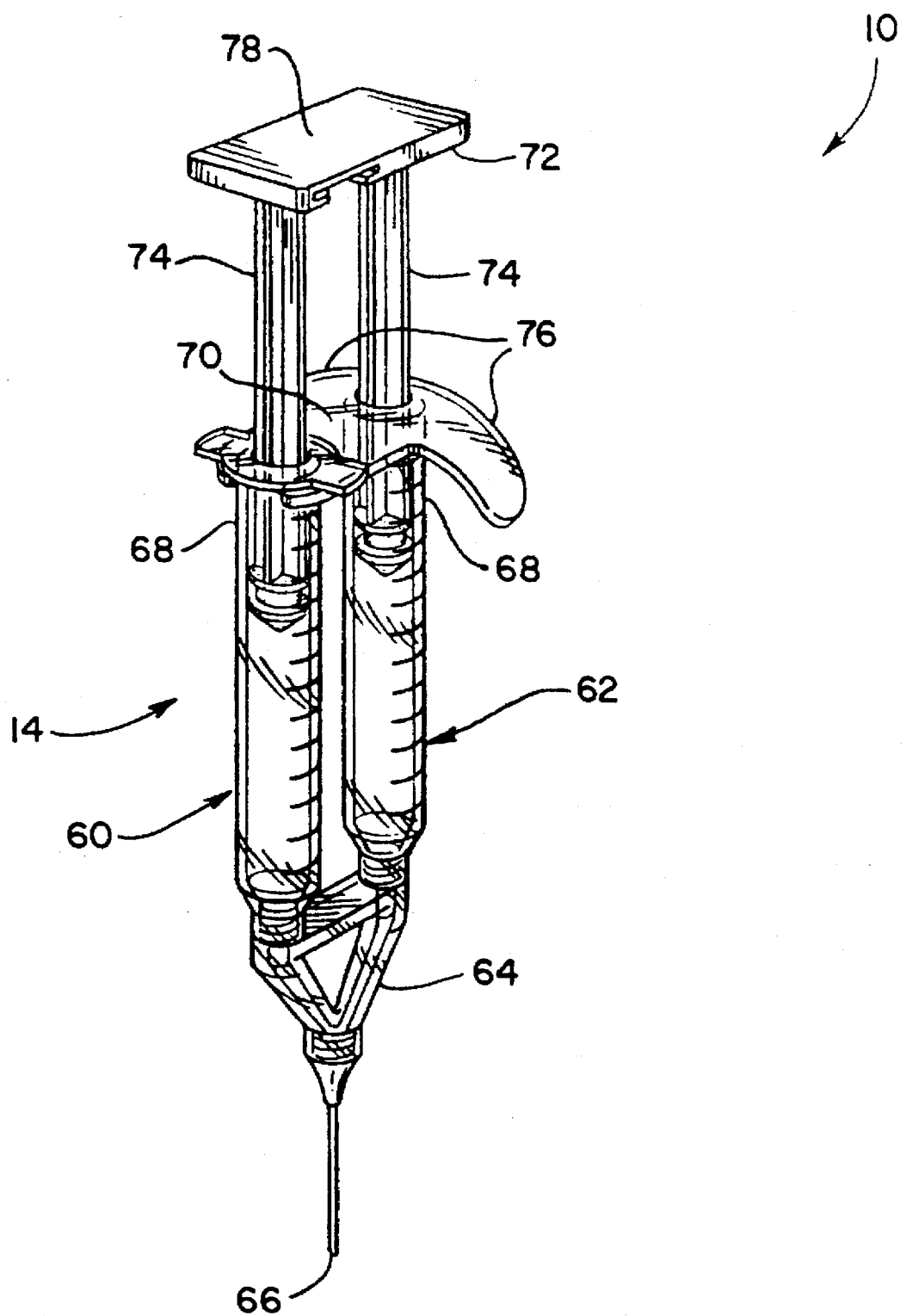
FIG. 4 is a perspective view of a fibrin gel applicator according to the invention.

Turning now to the drawings, FIGS. 1 and 4 illustrate a system 10 for preparing fibrin gel from autologous plasma. The system 10 comprises in gross a plasma separator 12 (FIG. 1) and a fibrin gel applicator 14 (FIG. 4).

Concentrating on FIG. 1, the plasma separator comprises a filter unit 16, a first retentate syringe 18 at a filter unit first end 20 and a second retentate syringe 22 at a filter unit second end 24. A collection syringe 26 affixes to a central portion 28 of the filter unit 16. Each of the syringes 18, 22 and 26 is of a type commonly used in the medical field and comprises a tubular body 30, a plunger 32 with an elastomeric head 34, and a Luer fitting 36 on the syringe body 30.

Figure 2:
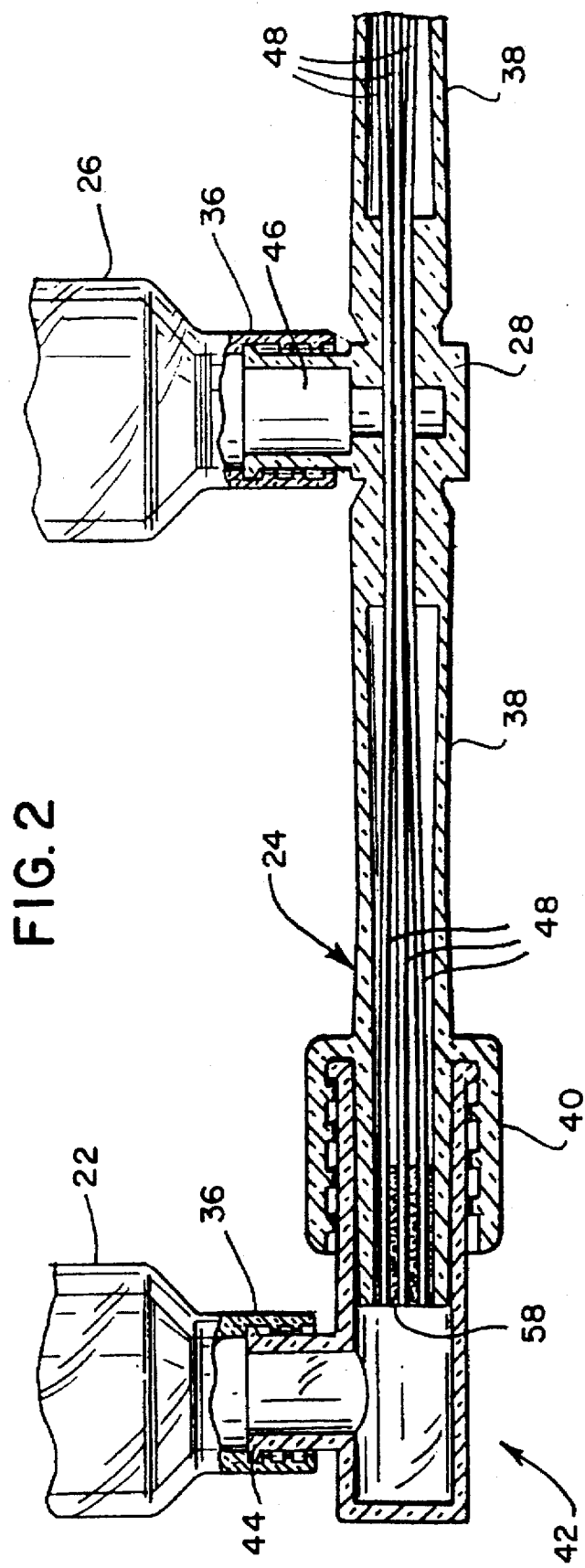
FIG. 2 is a sectional view taken along lines 2—2 of FIG. 1.
Figure 3:
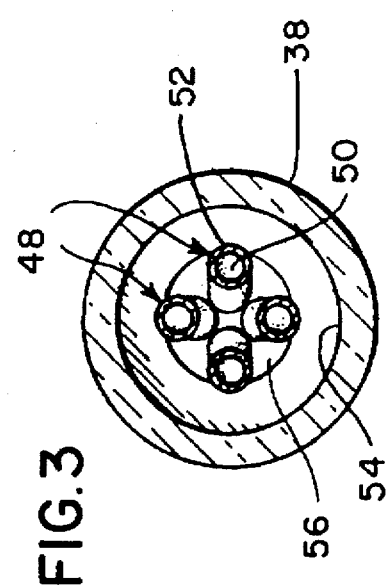
FIG. 3 is a sectional view taken along lines 3—3 of FIG. 1.

Turning now to FIGS. 2 and 3, the filter unit 16 comprises an elongated tubular housing 38 having female luer fittings 40 at its first and second ends 20 and 24. A right angle adapter 42 connects to each of the luer fittings 40 and provides a male luer fitting 44 for receiving the retentate syringes 18 and 22. A central fitting 46 is provided in the filter unit central portion 28 and receives the collection syringe 26.

One of skill in the art will appreciate that the retentate syringes 18 and 22 may attach to the housing 38 in various other fashions and orientations. For instance, appropriate mating luer fittings (not shown) may be provided at the filter unit first and second ends 20 and 24 for directly receiving the retentate syringes 18 and 22 without the need for separate adapters 42, and of course the retentate syringes 18 and 22 may be axially oriented with respect to the housing 38.

A plurality of hollow fiber filter membranes 48 extend axially through the housing 38. As best seen in FIG. 3, each of the fibers 48 has an interior lumen 50 and outer surface 52. The housing 38 has an interior surface 54 and an interior space 56 is defined between the fiber outer surfaces 52 and the housing inner surface 54. A plug or potting 58 at each of the filter unit first and second ends 20 and 24 retains the fibers 48 within the housing 38 and separates the lumens 50 from the interior space 56.

Preferably, the housing 38 is formed of polysulfone and the potting 58 is formed of polyurethane. Of course, other materials suitable for use in medical devices may be substituted therefor. Preferably, the parts housing 38 is formed as a single unit, or if formed of separate parts is bonded using sonic welding to avoid the use of solvent bonding. The fibers 48 are preferably formed of a mixed cellulose ester membrane, polysulfone membrane, or other suitable material as is known in the art.

The pores (not shown) in the membrane fibers 48 are preferable sized to pass blood plasma without allowing erythrocytes or leukocytes to pass. The membrane pore size may or may not exclude blood platelets. For instance, the fibers 48 having a maximum pore size of 0.55 microns, a lumen diameter of 0.3 to 1.0 mm, a lumen length of 9.0 cm and a total membrane surface area of at least 4 square cm provides sufficient separation of plasma from whole blood without causing undo hemolysis. Preferably, flow through the fibers 48 is laminar. Sufficient surface area is important to achieving relatively quick separation of plasma from whole blood. Preferably, about 2 ml of plasma should be separable from 4 ml of whole blood in about 2 minutes.

Turning to FIG. 4, the fibrin gel applicator 14 may be of any type commonly know for simultaneously applying blood plasma along with a solution of thrombin. The Wolff et al. U.S. Pat. No. 5,104,375, issued Apr. 14, 1992, discloses a locking holder for a pair of syringes and a method for using the syringes to simultaneously apply blood plasma and a solution of thrombin to produce fibrin gel. The disclosure of this patent is incorporated by reference.

The applicator 14 comprises a first injector syringe 60 for containing a solution of thrombin, and a second injector syringe 62 for containing blood plasma. Each of the first and second injector syringes 60 and 62 connects to a manifold 64 which directs the flow of thrombin solution and plasma to a distal outlet 66. Proximal ends 68 of the first and second injector syringes 60 and 62 are connected by a brace 70 which holds the first and second injector syringes 60 and 62 in parallel relationship to one another. A bridge 72 interconnects plungers 74 in the first and second injector syringes 60 and 62. A finger rest 76 extends laterally from the brace 70 for easy engagement by a user's index and middle finger and an upper surface 78 of the bridge 72 easily engages a user's thumb, whereby both the first and second injector syringes 60 and 62 may be easily actuated in a single-handed operation.

Each of the components of the system 10 which come into contact with whole blood or plasma should be treated with an anticoagulant such as sodium citrate, EDTA, or heparin to prevent premature clot formation. Thus, the syringes 18, 22 and 26, the filter unit 16 and the fibrin applicator 14 should preferably be treated with an anticoagulant.

The plasma separator 12 and fibrin applicator 14 are most conveniently provided in a sterile condition within a sterile package (not shown) containing instruction for obtaining whole blood from a patient, separating plasma from the whole blood, and applying the plasma and the thrombin solution simultaneously to produce fibrin gel. In such an arrangement, the first retentate syringe 18 has a standard blood collection needle tip (not shown) and contains an anticoagulant. For instance, a 10 ml syringe preferably contains 0.1 ml of a 46.7% trisodium citrate anticoagulant. Also, the collection syringe 26 preferably serves as the first injector syringe 60. Thrombin and a hemostatic agent to overcome the anticoagulant are provided for use in the second injector syringe 62. Preferably, 1000 units of thrombin in 9 ml of normal saline plus 0.5 ml of a 10% calcium chloride solution are mixed and packaged within the second injector syringe 62.

In use, a quantity of whole blood is withdrawn from a patient using the first retentate syringe 18 with the trisodium citrate therein. The needle is removed from the first retentate syringe 18 and its luer fitting 36 connected to the luer fitting 40 at the filter unit first end 20. The second retentate syringe 22 is similarly affixed to the filter unit second end 24. The collection syringe 26 is then affixed to the central fitting 46. By alternatingly depressing the plungers 32 on the first and second retentate syringes 18 and 22, the blood is forced to flow back and forth through the lumens 50 of the membrane fibers 48. This flow and a resulting slightly elevated pressure within the lumens 50 causes the plasma in the blood to migrate across the fibers 48 and into the interior space 56. The central fitting 46 is in fluid communication with the interior space 56 and thus receives the blood plasma.

After a sufficient amount of plasma has been accumulated in the collection syringe 26, it is removed from the filter unit 16 and inserted into the manifold 64 of the fibrin applicator 14. The solution of thrombin containing calcium chloride and the blood plasma are then simultaneously applied to a site on the body with the fibrin applicator 14. As the plasma and thrombin solutions mix, they create a fibrin gel which can be used in any number of medical procedures.

In one test, disposable tangential flow filtration units such as the filter unit 24 were used to separate plasma from canine blood. The plasma was collected within a few minutes and when combined with thrombin, formed a cohesive gelatinous clot. Clot formation as measured in a fibrinometer occurred in less than one second. In a second test, a 0.2 micron filter was used, and 1.8 ml of plasma was easily separated from approximately 4.0 ml of whole citrated porcine blood in two minutes. Clotting characteristics were similar to the first experiment.

While the invention has been described with regard to a particular embodiment thereof, those skilled in the art will understand, of course, that the invention is not limited thereto since modifications can be made by those skilled in the art, particularly in light of the foregoing teachings. Reasonable variation and modification are possible within the foregoing disclosure of the invention without the departing from the spirit of the invention.

What is claimed is:

1. A single use system for obtaining autologous plasma comprising a plasma separator for separating plasma from whole blood, the plasma separator comprising:

a single use filter unit comprising a first inlet and a second inlet in fluid communication with each other, an outlet, and a filtration membrane separating the inlets from the outlet, the filtration membrane being selectively permeable to blood plasma;

a manually operable, single use first pump comprising a first receiving chamber connected to the first inlet, the first receiving chamber being defined in part by a manually moveable first wall wherein movement of the first wall alters the volume of the first receiving chamber;

a manually operable, single use second pump comprising a second receiving chamber connected to the second inlet, the second receiving chamber being defined in part by a manually moveable second wall wherein movement of the second wall alters the volume of the second receiving chamber; and a flow path along the membrane between the first and second pumps;

whereby to repeatedly exchange whole blood between the first and second receiving chambers past the membrane, whereby to allow plasma to flow across the membrane and out of the outlet.

2. A system according to claim 1 wherein the membrane comprises one or more hollow fibers, each of the one or more fibers having a lumen therethrough, and the flow path extends through the lumens of the one or more fibers.

3. A system according to claim 2 wherein the filter unit comprises:

an elongated housing having a first end and a second end with the one or more hollow fibers extending axially therethrough;

each of the one or more fibers having an outer surface, the housing having an inner surface and an interior space being formed between the outer surfaces of the one or more fibers and the inner surface of the housing;

pottings at the first and second ends of the housing for securing the one or more fibers therein and for separating the lumens from the interior space;

the first pump being connected to the housing first end with the first receiving chamber in fluid communication with the lumens of the one or more hollow fibers;

the second pump being connected to the housing second end with the second receiving chamber in fluid communication with the lumens of the one or more hollow fibers; and the outlet being in fluid communication with the interior space;

whereby when the blood is pumped through the lumens of the one or more hollow fibers by the first and second pumps, the plasma flows through the membrane into the interior space of the housing and out of the outlet.

4. A system according to claim 3 wherein the one or more hollow fibers have a total surface area of at least 3 square cm and a lumen diameter of between 0.3 to 1.0 mm.

5. A system according to claim 2 wherein the first and second pumps comprise first and second retentate syringes, respectively.

6. A system according to claim 5 further comprising a collection syringe connected to the outlet for receiving the plasma.

* * * * *